United States Patent [19]
Swing

[11] Patent Number: 5,861,016
[45] Date of Patent: Jan. 19, 1999

[54] METHOD OF WOUND HEALING USING ELECTRICAL STIMULATION AND ACUPUNCTURE NEEDLES

[76] Inventor: Fred P. Swing, 24010 Harborview Rd., Charlotte Harbor, Fla. 33980

[21] Appl. No.: 864,307

[22] Filed: May 28, 1997

[51] Int. Cl.$^6$ ..................................................... A61N 7/34
[52] U.S. Cl. ............................................................... 607/50
[58] Field of Search .............................................. 607/50

[56] References Cited

U.S. PATENT DOCUMENTS

| | | | |
|---|---|---|---|
| 4,738,250 | 4/1988 | Fulkerson et al. | 607/50 |
| 5,158,081 | 10/1992 | McWhorter et al. | 607/50 |
| 5,607,461 | 3/1997 | Lathrop | 607/50 |

FOREIGN PATENT DOCUMENTS

| | | | |
|---|---|---|---|
| 3006797 | 9/1980 | Germany | 607/50 |

*Primary Examiner*—William E. Kamm
*Attorney, Agent, or Firm*—Stroock & Stroock & Lavan LLP

[57] ABSTRACT

A method for healing a wound of a patient using an electrical stimulator and acupuncture needles is provided. The method includes the step of positioning a plurality of acupuncture needles coupled to the electrical stimulator substantially around the wound. The next step includes applying a current to the acupuncture needles positioned substantially around the wound. The first half of the treatment, a current is applied through the needles until a stinging sensation (or pain) is felt by the patient. Halfway through the treatment, the current is increased until a stinging sensation is again felt by the patient. At least four acupuncture needles are substantially positioned around the wound and alternating the polarity of the needles. The needles are further separated by one-half to two inches from the wound.

6 Claims, 2 Drawing Sheets

METHOD OF WOUND HEALING USING ELECTRICAL STIMULATION AND ACUPUNCTURE NEEDLES

BACKGROUND OF THE INVENTION

This invention relates generally to a method of healing a wound, and more particularly to a method of healing a wound using electrical stimulation and acupuncture needles.

While electrical stimulators are well known in the art, they are typically used in conjunction with Traditional Chinese Medicine meridians ("TCM"). TCM is an ancient procedure that uses 250 different points, which are points of lesser electrical resistance on the human body, to cure various medical conditions. That is, acupuncture needles are inserted at these predetermined points on TCM meridians (lines) and then left alone for a period of time or stimulated by a variety of methods:

1. manually manipulating the needles;
2. heat applied to the needles (moxa—similar to a hot lighted end of a cigar); and
3. an electrical current.

In addition, the Craig PENS theory and treatment is well-known in the art. The PENS method follows dermatomes, myotomes and neurotomes of the human body which are found in various anatomy books. Similar to TCM, the acupuncture needles are positioned at pre-defined locations on the human body associated with specific muscles, nerves or the like to dissipate pain. Craig PENS is used for pain treatments only—back pain; neck pain; joint pain, etc.

Accordingly, prior art methods fail to teach the use acupuncture needles to heal a wound irrespective of the specific pressure points or Chinese meridian points on the human body. To overcome this deficiency, the present invention uses acupuncture needles and positions them with specific reference to the location of the wound.

SUMMARY OF THE INVENTION

Generally speaking, in accordance with the invention, a method for healing a wound of a patient using an electrical stimulator is provided. The method includes the step of positioning a plurality of acupuncture needles coupled to the electrical stimulator substantially around the wound. The next step includes applying a current to the acupuncture needles positioned substantially around the wound. During the first half of the treatment, a current is applied through the needles until a stinging sensation is felt by the patient. Halfway through the treatment, the current is increased until a stinging sensation is again felt by the patient. At least four acupuncture needles are substantially positioned around the wound and alternating the polarity of the needles. The needles are further separated by one-half to two inches from the wound.

Accordingly, it is an object of the invention to provide an improved method of healing wounds using electrical stimulation and acupuncture needles.

Another object of the invention is to provide a method for wound healing using acupuncture needles irrespective of TCM or the specific muscle, nerve or skin locations.

A further object of the invention is to provide a method for healing wounds by using acupuncture needles for receipt of an electrical current and positioning such needles at specific locations substantially about the wound.

Still other objects and advantages of the invention will in part be obvious and will in part be apparent from the specification.

The invention accordingly comprises the several steps and the relation of one or more of such steps with respect to each of the others thereof, which will be exemplified in the method hereinafter disclosed, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
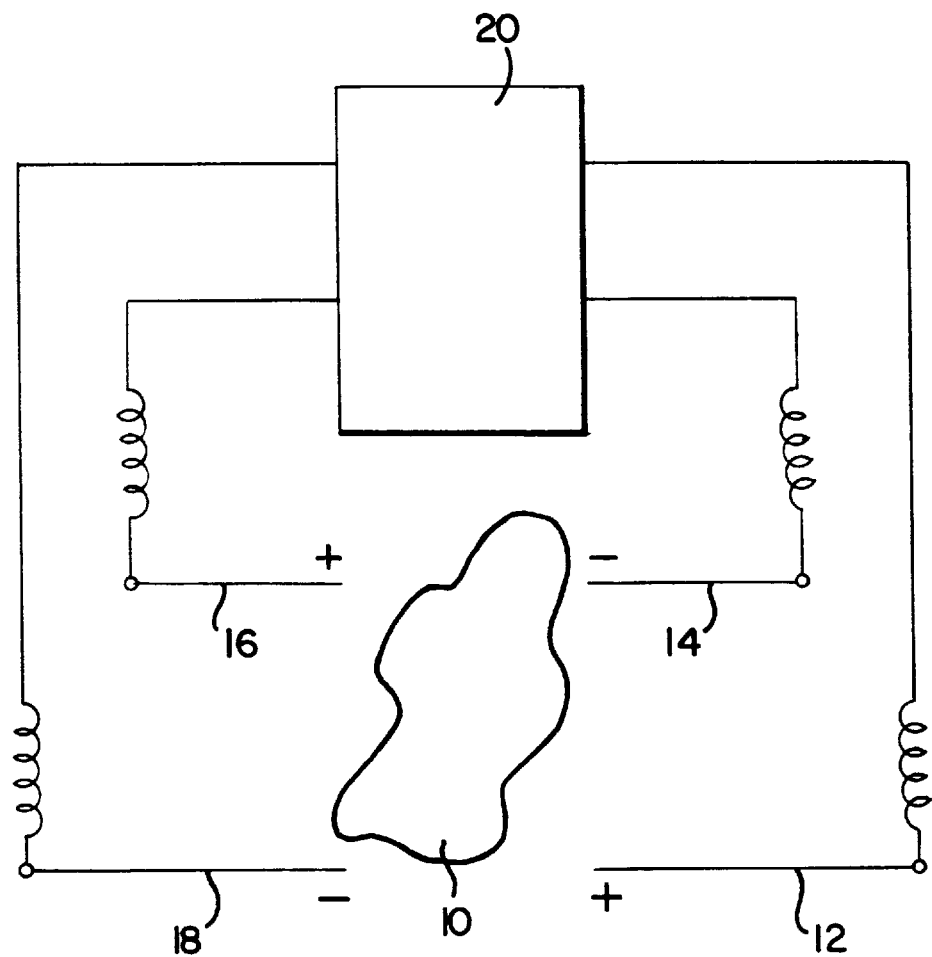
FIG. 1 is a schematic of the apparatus used to heal a wound.
Figure 2:
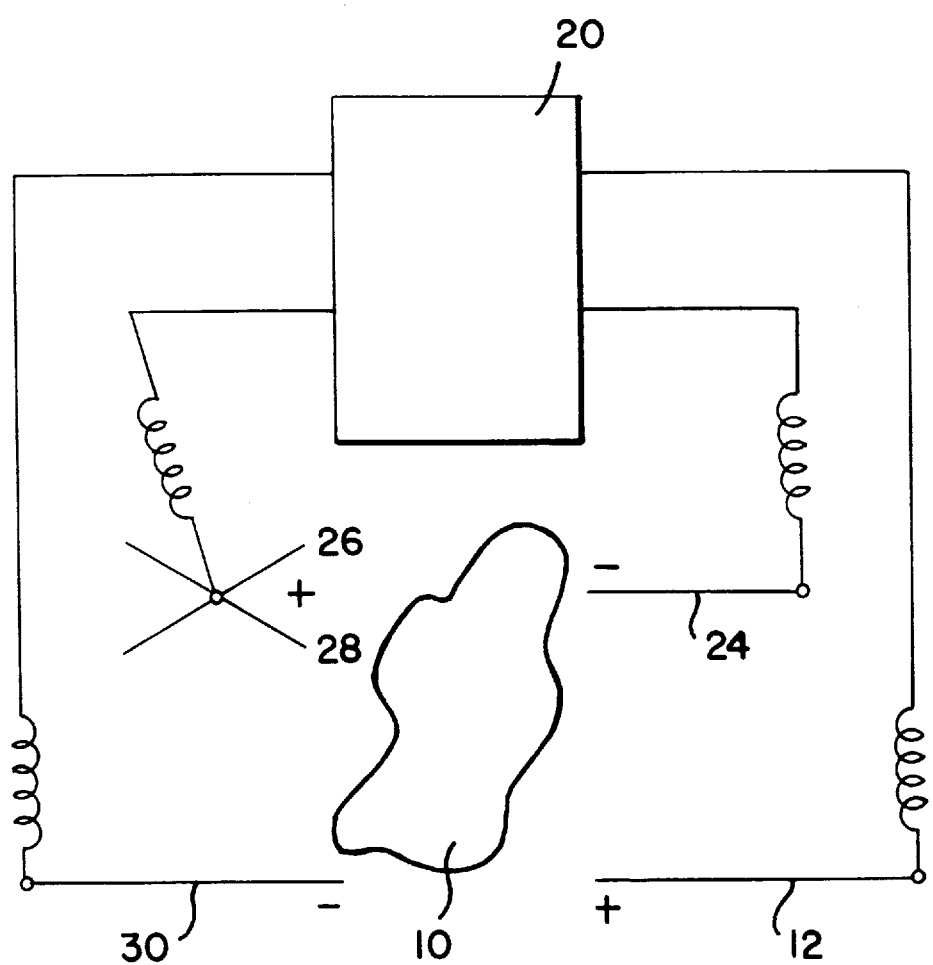
FIG. 2 is a schematic of another embodiment of an apparatus used to heal a wound.

Referring to FIG. 1, a schematic used to heal a wound using electrical stimulation is generally shown. A wound 10 is substantially surrounded by acupuncture needles 12, 14, 16 and 18. While four acupuncture needles are used, any combination of needles may be used and preferably in the range of 4–8 so long as it properly encircles the wound. Needles of different polarity reside in proximity of one another so that, for example, two positive or two negative needles are not adjacent. Preferably, needles 12, 14, 16 and 18 are approximately two inches from one another and are positioned approximately ½ to two inches from wound 10. Sometimes the shape of a wound is such that two acupuncture needles replace one acupuncture needle as shown in FIG. 2. Needles 22, 24 and 30 are positioned in the same manner as described above with respect to FIG. 2. However, needles 26 and 28 are placed ½ to one inch from each other and are crossed near the top of the needles so one electrode can attach to both needles.

Needles 12, 14, 16 and 18 as well as needles 22, 24, 26, 28 and 30 are connected to an electrical stimulator 20. Electrical acupuncture stimulators 20 are well known in the art. For example, Electrotherapeutic Devices, Inc. of Markham Ontario, Canada sells a Multiple Electronic Acupunctoscope Model G6805 and Ito Co., Ltd. of Japan sells an Electropuncture IC1107 model. Electrical stimulator 20 is designed for clinical use and transmits pulsating currents of different intensities and frequencies through the acupuncture needles to the human body.

Electrical stimulator 20 is coupled to needles 12, 14, 16 and 18 alternating between the positive and negative leads so that a positive needle does not reside immediate adjacent to a negative needle and vice versa. Traditional acupuncture lines such as traditional Chinese meridians are not used. Rather, as set forth above, the needle placement is based solely on the size of the wound and the positioning of the various needles with respect to one another. To heal the wound, electrical stimulator 20 is turned on and the current is increased until the needles stings or begins to hurt the patient. A four hertz frequency is preferably used to apply the current. The current depends on the frequency of the electrical stimulator being used, but is preferably in the range of 1 Hz to 25 Hz However, any frequency in the range of one to twenty-five Hz may be used depending on the individual, the size of the wound and other such issues.

Halfway through the treatment, which lasts 20 to 30 minutes, the current is again increased until it starts to sting or begins to hurt the patient. The above method is repeated 3–5 times a week. Treatments are continued until wound healing is complete or almost complete in smaller wounds or until in bigger wounds the wound bed has enough granulation tissue (growth of blood vessels) covering the wound so a skin graft can be done. After the skin graft is done, acupuncture treatments may be continued for 1–2 weeks to increase graft survival.

Based on the application of the current to the blood vessels in the vicinity of the wound, the blood flow is increased to the wound, thereby decreasing the healing time (making shorter the healing time). By increasing the blood flow in and around the area of the wound, it makes it possible for more oxygen and body nutrients to get to the wound thereby allowing the wound to heal much quicker and can change non-healing wounds to healing wounds.

Example

An individual sustained an insect bite on the lower left leg. The wound appeared as a two centimeter, red, raised area with a fluid-center approximately one centimeter in size. After three days, it was opened and drained. Thereafter, the red area enlarged to five centimeters in size and the pain increased at the wound site and spread to cover the leg area from the knee down to the ankle. The wound was treated with normal saline rinse and clean dry dressing twice a day. The necrotic center gradually enlarged. Five days after the initial bite, the patient started taking Augmentin and Dapsone orally prescribed by a physician. Three days thereafter the pain was increasing and was interfering with walking.

Seven days from the original bite, another doctor initiated an IV Vancomycin for twelve days with whirlpool and debridement by physical therapy. Three days later, celulitis set in and the patient was restarted on IV Vancomycin for five days. More than a month later, while the celulitis and infection cleared up, the wound remained open with no further healing. Shortly thereafter, the ulcer (wound) was two to three millimeters deep and the diameter was approximately 2½ to 3 centimeters. The patient had indicated that there had been no change in the size of the ulcer for more than three weeks.

As a result, the method described above was applied in which four needles 12, 14, 16 and 18 were placed around the wound, with alternating polarity separating each needle. The needles were spaced two inches apart from one another and were positioned ½ to 2 inches away from the wound. Electrical stimulator 20 was activated using a frequency of 4 hertz. A current was applied until a stinging pain was felt by the patient. Halfway through the treatment, approximately ten minutes into the treatment, the current was increased until a stinging pain was again felt by the patient. This process lasted approximately 20 minutes in total. As a result of the application, the cyanotic (blue) rim around the wound became pink and 12 hours after the first acupuncture treatment 95% of the pain disappeared.

By the fourth treatment which occurred seven days after the original treatment, the ulcer diameter had decreased by two millimeters and the entire base of the wound (ulcer) had filled in with granulation tissue. In another 5 days, a scab formed over the wound and in another 5 days the scab fell off—the wound (ulcer) completely healed 17 days from the first acupuncture treatment. Based on the application of the method described above, the treatment destroyed the toxin from the bite and broke up the Vasospasm (constricted blood vessel) on the rim of the ulcer, thus allowing the ulcer to heal.

The same method may be used as described above, for non-healing skin ulcers, diabetic non-healing skin ulcers and peripheral vascular disease non-healing skin ulcers and or any skin wound not healing due to decreased blood flow in the area of the wound.

It will thus be seen that the objects set forth above, among those made apparent from the preceding description, are efficiently attained and, since certain changes may be made in carrying out the above method without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A method of healing a wound of a patient using an electrical stimulator, comprising the steps of:
    positioning substantially around the wound a plurality of acupuncture needles coupled to the electrical stimulator; and
    applying a current through the acupuncture needles positioned about the wound.

2. The method of claim 1, further including the step of increasing the current through the acupuncture needles to the wound until a stinging sensation is felt by the patient.

3. The method of claim 1, where said positioning of acupuncture needles around the wound includes the step of inserting at least 4 acupuncture needles around the wound and alternating the polarity of said needles.

4. The method of claim 3, further including the step of separating the acupuncture needles by about two inches from one another.

5. The method of claim 4, wherein the at least 4 needles are inserted about 0.5 to 2.0 inches from the wound.

6. The method of claim 5, further including the step of increasing the current through the acupuncture needles to the wound until a stinging sensation is felt by the patient.

* * * * *